United States Patent [19]

Wang et al.

[11] 4,310,541

[45] Jan. 12, 1982

[54] METHOD OF TREATING GIARDIASIS AND TRICHOMONIASIS

[75] Inventors: Ching C. Wang, Watchung; Nancy J. Dick, Colts Neck, both of N.J.

[73] Assignee: Merck & Co., Inc., Rahway, N.J.

[21] Appl. No.: 189,415

[22] Filed: Sep. 22, 1980

[51] Int. Cl.³ .......................................... A61K 31/275
[52] U.S. Cl. ................................. 424/304; 424/300
[58] Field of Search ............................. 424/304, 326

[56] References Cited

U.S. PATENT DOCUMENTS

| | | | |
|---|---|---|---|
| 3,769,432 | 10/1973 | Tomcufcik | 424/326 |
| 3,901,944 | 8/1975 | Tomcufcik | 260/564 F |
| 3,941,825 | 3/1976 | Tomcufcik | 260/465 E |
| 3,992,446 | 11/1976 | Tomcufcik | 260/564 F |

OTHER PUBLICATIONS

Altman, L. K., The New York Times, Jun. 10, 1980, p. C-1.
Dykers, Medical Intelligence, vol. 293, pp. 23-24, (1975).
Kerlin et al., Digestive Diseases, vol. 23, pp. 940-942, (1978).
Hartong et al., Gastroenterology, vol. 77, pp. 61-69, (1979).
Craun., The American Journal of Public Health, vol. 69, pp. 817-819, (1979).
Fouts et al., The Journal of Infectious Diseases, vol. 141, pp. 137-143, (1980).
Wisdom, et al., The British Journal of Venereal Diseases, vol. 41, pp. 90-96, (1965).
Naguib, et al., The Journal of Obstetrics and Gynecology, vol. 27, pp. 607-616, (1966).
Hughes et al., Journal of Obstetrics and Gynecology of the British Commonweath, vol. 73, pp. 821-827, (1966).
Ings et al. Biochemical Pharmacology, vol. 23, pp. 1421-1429, (1974).
Collection of Monographs from International Conference of the Chemistry, Pharmacology, and Clinical Application of Nitroimidazoles, Aug. 1980, pp. 33-36, 53-54, 61-62 and 67.

*Primary Examiner*—Frank Cacciapaglia, Jr.
*Attorney, Agent, or Firm*—David L. Rose; Harry E. Westlake

[57] ABSTRACT

Benzylidene aminoguanidene derivatives, known as effective anti-coccidial agents, are useful as potent anti-giardiasis and anti-trichomoniasis agents.

3 Claims, No Drawings

METHOD OF TREATING GIARDIASIS AND TRICHOMONIASIS

BACKGROUND OF THE INVENTION

*Giardia lamblia*, a parasite that until recent years was believed by most physicians to be harmless, now heads the list of the most common intestinal parasitic infections in the United States and some other countries. The parasite causes a diarrheal disease called giardiasis.

The parasite can infect anyone, anyplace, and it causes a variety of intestinal symptoms, such as prolonged diarrhea, abdominal cramps, stomach pain, severe weight loss, fatigue, nausea and flatulence.

Giardiasis can cause malabsorption of nutrients and even retarded growth. More importantly, giardiasis can mimic the symptoms of other conditions such as ulcers and gall bladder attacks. A patient may have a series of costly, needless tests, and even surgery, unless the physician considers the parasite as a possible diagnosis.

Usually the infection can be successfully treated with one of three drugs: Atabrine, Flagyl or furazolidone. However, each of these drugs is known to cause adverse side effects. Until the present invention, no prophylactic drug has been found which can successfully protect against giardiasis. (L. K. Altman, M.D., *The New York Times*, June 10, 1980).

The present invention relates to the use of a group of benzylidene aminoguanidines which are more active and less toxic than Flagyl (metronidazole) and other commonly used drugs in the treatment of giardiasis in humans. Flagyl is a known carcinogen whereas the benzylidene aminoguanidines have been established as a safe anticoccidial drug.

The benzylidene aminoguanidines and methods of preparation thereof have been disclosed in U.S. Pat. Nos. 3,769,432; 3,901,944; 3,941,825; and 3,992,446, and are herein incorporated by reference.

The utilities disclosed in these patents are essentially (1) control of coccidiosis and (2) preventing or treating malaria in chickens and other domestic animals such as turkeys, sheep, cattle and pigs. The causative microorganisms of coccidiosis are of the genus Eimeria and that of malaria are of the genus Anopheles.

SUMMARY OF THE INVENTION

The present invention is directed to the novel method for control and treatment of giardiasis, a parasitic infection in humans caused by a protazoa of the genus Giardia. As reported in the New York Times article, cited above, there has been yet no drug which can protect against giardiasis.

The novel compositions used in the present method are also active as anti-trichomoniasis agent in humans. Although successful therapy of trichomoniasis with Flagyl (metronidazole) has been reported, the drug has the serious side effect of being a known carcinogen.

Therefore, it is the object of the present invention to (1) provide novel compositions comprising a benzylidene aminoguanidine derivative with anti-giardiasis and anti-trichomoniasis activities; (2) provide a novel method for the prevention, control and/or treatment of giardiasis and trichomoniasis in humans through the administration of these novel compositions.

DETAILED DESCRIPTION OF THE INVENTION

The benzylideneaminoguanidines to be used in the methods and compositions of the present invention have the structural formula:

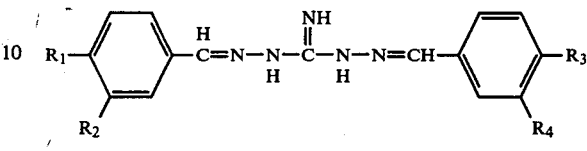

or a pharmaceutically acceptable salt thereof, wherein $R_1$ and $R_3$ are independently
 (a) halogen such as chlorine, bromine, fluorine, or iodine;
 (b) trifluoromethyl or
 (c) cyano; and $R_2$ and $R_4$ are independently
 (a) hydrogen or
 (b) halogen as previously described.

These benzylidene aminoguanidines and the method of preparation thereof are disclosed in U.S. Pat. Nos. 3,769,432; 3,901,944; 3,941,825; and 3,992,446.

The prefered benzylidene aminoguanidines are selected from the following compounds:
 (1) 1,3-bis(4-chlorobenzylideneamino)guanidine (robenidine)
 (2) 1,3-bis(4-bromobenzylideneamino)guanidine
 (3) 1,3-bis(3,4-dichlorobenzylideneamino)guanidine
 (4) 1,3-bis(4-cyanobenzylideneamino)guanidine
 (5) 1-(4-bromobenzylideneamino)-3-(4-cyanobenzylideneamino)guanidine
 (6) 1-(4-bromobenzylideneamino)-3-(4-chlorobenzylideneamino)guanidine
 (7) 1-(4-chlorobenzylideneamino)-3-[4-(trifluoromethyl)benzylideneamino]guanidine.

The pharmaceutically acceptable salts of the above compounds are, for example, hydrohalides such as hydrochloride, hydrobromide; nitrate; fluorosulfate; sulfate or methosulfate; phosphate; or salts resulting from the neutralization of the base with an organic acid such as maleic, fumaric, tartaric, citric, acetic, salicylic, succinic, benzoic, benzenesulfonic, glutamic or lactic acid. Such salts are equally active anti-giardiasis or anti-trichomoniasis agents.

The activity of these compounds against *Giardia lamblia* and *Trichomonas vaginalis* are shown by the following test:

About 1.0–2.0 ml of a nutrient medium, for example, the modified Diamond's (TPS) medium at pH 7.05, together with about 10% by volume of heat-inactivated serum and about 1% by volume of a penicillin-streptomycin antibiotic mixture, is placed in each well of a multiwell plate. To this mixture, an aliquot of a suspension of *G. lamblia* cells containing about $10^6$ organisms is added. Subsequently, each well is inoculated with a known concentration of one of the benzylidene aminoguanidines, for example, 1,3-bis(4-chlorobenzylideneamino)guanidine (robenidine). The multiwell plate containing the individual culture samples is incubated under anaerobic conditions at about 37° C. for about 16–24 hrs. The number of viable cells remaining in each well are then counted, such as with a hemacytometer. The percentage of survival is determined by comparison to controls inoculated with DMSO (dimethylsulfoxide) and the effective concentration (in parts per million) for 50% inhibition of growth ($ED_{50}$) is determined. It is established that the lower the $ED_{50}$, the higher the activity of the benzylideneaminoguanidine tested. Robenidine ($ED_{50}=1.5$ ppm) is found to be about 4 times more active than Flagyl (metronidazole) ($ED_{50}=6.2$ ppm) in inhibiting the growth of *Giardia lamblia;* and is about one third as active as flagyl in the treatment of trichomoniasis.

The present method comprises the administration of an active compound, for example, 1,3-bis(4-chlorobenzylideneamino)guanidine, as an anti-giardiasis or anti-trichomoniasis agent to a human patient in amounts ranging from about 0.05 to about 50 mg. per kg. of body weight, preferably from about 0.25 to about 25 mg. per kg. of body weight in a single dose or in 2 to 4 divided doses.

These compounds in the described dosages are usually administered orally. They may also be administered to individuals by injection. The oral pharmaceutical compositions of this invention usually consist of an active compound and some appropriate excipients and used in the form of tablets, troches, capsules, elixirs, suspensions, syrups, wafers, chewing gums and the like. The amount of an active compound in such a therapeutically useful composition or preparation usually ranges from about 2.5 mg. to about 2.5 g, preferably from about 5 mg. to about 500 mg. per unit dosage.

The previously described tablets, troches, capsules, pills and the like usually contain one or more of the following inactive ingredients: a binder such as gum tragacanth, acacia, corn starch or gelatin; an excipient such as dicalcium phosphate; a disintegrating agent such as corn starch, potato starch, alginic acid and the like; a lubricant such as megnesium stearate; and a sweetening agent such as sucrose, lactose or saccharin and/or a flavoring agent such as peppermint, oil of wintergreen, or cherry flavoring. When the dosage unit form is a capsule, it may contain in addition to materials of the above type, a liquid carrier such as fatty oil. Various other materials may be present as coatings or to otherwise modify the physical form of the dosage unit, for instance, tablets, pills, or capsules may be coated with shellac, sugar, or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially nontoxic in the amounts employed.

EXAMPLE 1

In each well of a multiwell plate is placed 1.4 ml of Diamond's TPS medium (See Table I) at pH 7.05, 10% by volume of heat-inactivated fetal bovine scrum, and 1% by volume of an antibiotic-antimycotic solution (see Table II). A suspension of *Giardia Lamblia* is centrifuged at 2,500 xg for 6 minutes. The pelleted cells are re-suspended in a small volume of Diamond's medium, the cells are counted and each well inoculated with approximately $10^6$ organisms. A stock solution of robenidine in dimethylsulfoxide is made at a concentration of 150 μg/ml. The wells are then inoculated with various concentrations of the drug. The plates are incubated for 24 hours at 37° C. in an anaerobic Gas Pak jar. After 24 hours of incubation, each well is mixed and counted for viable organisms using a haemacytometer. The percentage of survival is determined by comparing the treated wells to controls treated with dimethylsulfoxide. Following the above procedure, robenidine is found to have an $ED_{50}$ of 1.50 ppm against *Giardia lamblia.*

TABLE I

| Composition of Diamond's TPS Medium | |
|---|---|
| Ingredients | Amounts |
| Trypticase (BBL) | 1.00 g. |
| Panmede, liver digest P & B | 2.00 g. |
| Glucose | 0.30 g. |
| L-cysteine monohydrochloride | 0.10 g. |
| Ascorbic acid | 0.02 g. |
| Sodium chloride | 0.50 g. |
| Potassium phosphate. monobasic | 0.06 g. |
| Potassium phosphate dibasic, anhydrous | 0.10 g. |
| Water, glass distilled to make | 87.30 ml. |
| pH adjusted to 7.0 with 1 N $N_aOH$ | |

TABLE II

| Antibiotic Antimycotic Solution (100X) | |
|---|---|
| Ingredients | Amounts |
| Penicillin | 10,000 units |
| Streptomycin | 10,000 mcg |
| Fungizone ® | 25 mcg |
| Prepared in normal saline | |

Employing essentially the same procedure as described above, but substituting for robenidine, i.e., 1,3-bis(4-chlorobenzylideneamino)guanidine, used therein, other benzilidineaminoguanidino compounds there are obtained similar results indicating activity against *G. lamblia* of the following compounds.

(2) 1,3-bis(4-bromobenzylideneamino)guanidine;
(3) 1,3-bis(3,4-dichlorobenzylideneamino)guanidine;
(4) 1,3-bis(4-cyanobenzylideneamino)guanidine;
(5) 1-(4-bromobenzylideneamino)-3-(4-cyanobenzylideneamino)guanidine;
(6) 1-(4-bromobenzylideneamino)-3-(4-chlorobenzylideneamino)guanidine;
(7) 1-(4-chlorobenzylideneamino)-3-[4-(trifluoromethyl)benzylideneamino]guanidine.

Similarly, following essentially the same procedure as described above, the hydrochloride salts of compounds (1) to (7) are found to be equally active as the corresponding free bases.

EXAMPLE 2

Employing the method of Example 1, centrifuged cells of *T. vaginalis* 30001 are incubated with robenidine at 37° C. for 24 hours. The results indicate that robenidine is also an effective anti-*T. vaginalis* agent with an $ED_{50}$ value of 3.13 ppm.

Similarly, compounds (2) to (7) and the pharmaceutically acceptable salts of compounds (1) to (7) are active against *T. vaginalis.*

EXAMPLE 3

| Preparation of Capsule Formulation | |
|---|---|
| Ingredient | Milligrams per Capsule |
| 1,3-bis(4-chlorobenzyl-ideneamino)guanidine | 10 |
| Starch | 100 |
| Magnesium stearate | 10 |
| Total weight | 120 mg. |

The active ingredient, starch and magnesium stearate are blended together. The mixture is used to fill hard shell gelatin capsules of a suitable size at a fill weight of 120 mg per capsule.

EXAMPLE 4

Preparation of Tablet Formulation

| Ingredient | Milligrams per Tablet |
|---|---|
| 1,3-bis(4-cyanobenzyl-ideneamino)guanidine | 12 |
| Lactose | 200 |
| Corn starch (for mix) | 50 |
| Magnesium stearate | 6 |

The active ingredient, lactose and corn starch (form mix) are blended together. The corn starch (for paste) is suspended in water at a ratio of 10 grams of corn starch per 80 milliliters of water and heated with stirring to form a paste. This paste is then used to granulate the mixed powders. The wet granules are passed through a No. 8 screen and dried at 120° F. The dry granules are passed through a No. 16 screen. The mixture is lubricated with magnesium stearate and compressed into tablets in a suitable tableting machine. Each tablet contains 12 milligrams of the active ingredient.

What is claimed is:

1. A method of treating giardiasis and trichomoniasis in humans which comprises the administration to a patient in need of such therapy an amount effective for the treatment of giardiasis and trichomoniasis of a benzylideneaminoguanidine of structural formula:

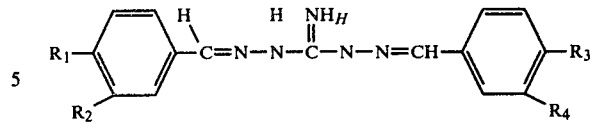

or a pharmaceutically acceptable salt thereof, wherein:
$R_1$ and $R_3$ are independently
  (a) halogen
  (b) trifluoromethyl or
  (c) cyano; and
$R_2$ and $R_4$ are independently
  (a) hydrogen or
  (b) halogen.

2. The method of claim 1 wherein $R_1$ and $R_3$ are independently
  (a) chlorine
  (b) bromine
  (c) trifluoromethyl or
  (d) cyano; and
$R_2$ and $R_4$ are independently
  (a) hydrogen or
  (b) chlorine or
  (c) bromine.

3. The method of claim 1 wherein the benzylidene aminoguanidine is selected from the group consisting of:
  (a) 1,3-bis(4-chlorobenzylideneamino)guanidine
  (b) 1,3-bis(bromobenzylideneamino)guanidine
  (c) 1,3-bis(3,4-dichlorobenzylideneamino)guanidine
  (d) 1,3-bis(4-cyanobenzylideneamino)guanidine
  (e) 1-(4-bromobenzylideneamino)-3-(4-cyanobenzylideneamino)guanidine
  (f) 1-(4-bromobenzylideneamino)-3-(4-chlorobenzylideneamino)guanidine
  (g) 1-(4-chlorobenzylideneamino)-3-[4-(trifluoromethyl)benzylideneamino]guanidine.

* * * * *